(12) United States Patent
Frigstad et al.

(10) Patent No.: US 9,949,811 B2
(45) Date of Patent: Apr. 24, 2018

(54) PELVIC IMPLANT AND THERAPEUTIC AGENT SYSTEM AND METHOD

(75) Inventors: John R. Frigstad, St. Anthony, MN (US); Thomas Q. Dinh, Minnetonka, MN (US); Emily R. Rolfes-Meyering, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 473 days.

(21) Appl. No.: 13/985,488

(22) PCT Filed: Feb. 23, 2012

(86) PCT No.: PCT/US2012/026325
§ 371 (c)(1),
(2), (4) Date: Nov. 4, 2013

(87) PCT Pub. No.: WO2012/116182
PCT Pub. Date: Aug. 30, 2012

(65) Prior Publication Data
US 2014/0088347 A1   Mar. 27, 2014

Related U.S. Application Data

(60) Provisional application No. 61/445,886, filed on Feb. 23, 2011.

(51) Int. Cl.
*A61F 2/02* (2006.01)
*A61F 2/00* (2006.01)
(Continued)

(52) U.S. Cl.
CPC .......... *A61F 2/0004* (2013.01); *A61F 2/0045* (2013.01); *A61L 31/16* (2013.01);
(Continued)

(58) Field of Classification Search
CPC .......................... A61L 33/007; A61L 33/0017
(Continued)

(56) References Cited

U.S. PATENT DOCUMENTS 3,560,601 A   2/1971   Johnson et al.
3,867,190 A   2/1975   Schmitt et al.
(Continued)

FOREIGN PATENT DOCUMENTS

WO   WO 2007/097994   8/2007
WO   WO 2008/057261   5/2008
(Continued)

OTHER PUBLICATIONS

Vermani et al., "The scope and potential of vaginal drug delivery," PSIT, vol. 3, No. 10, pp. 359-365 (Oct. 2000).
(Continued)

*Primary Examiner* — Catherine B Kuhlman
*Assistant Examiner* — Shannon McBride
(74) *Attorney, Agent, or Firm* — Brake Hughes Bellermann LLP

(57) ABSTRACT

Various embodiments of a mesh or implant system are provided for treating pelvic conditions such as incontinence, vaginal prolapsed, and other conditions caused by muscle and ligament weakness. Embodiments of the implants can include a material, substrate, configuration or coating adapted to provide immediate or timed release of various therapeutic agents or drugs to treat the surrounding tissue.

15 Claims, 6 Drawing Sheets

(51) Int. Cl.
*A61L 31/16* (2006.01)
*A61M 31/00* (2006.01)
*A61L 27/56* (2006.01)
*A61L 33/00* (2006.01)

(52) U.S. Cl.
CPC ........... *A61F 2/0031* (2013.01); *A61F 2/0036* (2013.01); *A61F 2/0063* (2013.01); *A61F 2/0077* (2013.01); *A61F 2/02* (2013.01); *A61F 2210/0076* (2013.01); *A61F 2250/0067* (2013.01); *A61F 2250/0068* (2013.01); *A61L 27/56* (2013.01); *A61L 33/007* (2013.01); *A61L 2300/602* (2013.01); *A61L 2300/604* (2013.01); *A61M 31/002* (2013.01)

(58) Field of Classification Search
USPC ........................................................ 606/151
See application file for complete search history.

(56) References Cited

U.S. PATENT DOCUMENTS

| | | | |
|---|---|---|---|
| 4,079,038 A | | 3/1978 | Choi et al. |
| 4,138,344 A | | 2/1979 | Choi et al. |
| 4,304,767 A | | 12/1981 | Heller et al. |
| 4,911,165 A | | 3/1990 | Lennard et al. |
| 5,051,259 A | | 9/1991 | Olsen et al. |
| 5,843,172 A | * | 12/1998 | Yan ................ 623/1.42 |
| 6,010,715 A | | 1/2000 | Wick et al. |
| 6,612,977 B2 | | 9/2003 | Staskin et al. |
| 6,648,921 B2 | | 11/2003 | Anderson et al. |
| 6,691,711 B2 | | 2/2004 | Raz et al. |
| 7,025,063 B2 | | 4/2006 | Snitkin et al. |
| 7,303,525 B2 | | 12/2007 | Watschke et al. |
| 7,347,812 B2 | | 3/2008 | Mellier |
| 7,351,197 B2 | | 4/2008 | Montpetit et al. |
| 7,407,480 B2 | | 8/2008 | Staskin et al. |
| 7,500,945 B2 | | 3/2009 | Cox et al. |
| 8,815,275 B2 | * | 8/2014 | Zhou ............... 424/423 |
| 2002/0090398 A1 | | 7/2002 | Dunn et al. |
| 2002/0147382 A1 | | 10/2002 | Neisz et al. |
| 2002/0151762 A1 | | 10/2002 | Rocheleau et al. |
| 2003/0033007 A1 | * | 2/2003 | Sirhan et al. ............ 623/1.42 |
| 2003/0181973 A1 | * | 9/2003 | Sahota ..................... 623/1.15 |
| 2005/0100582 A1 | * | 5/2005 | Stenzel .................... 424/426 |
| 2005/0100654 A1 | * | 5/2005 | Su et al. .................. 427/2.1 |
| 2006/0251702 A1 | * | 11/2006 | Janis et al. ............... 424/426 |
| 2007/0254012 A1 | * | 11/2007 | Ludwig et al. ........... 424/426 |
| 2008/0004490 A1 | * | 1/2008 | Bosley, Jr. ......... A61B 17/06109 600/37 |
| 2008/0009662 A1 | * | 1/2008 | Bartning ............. A61F 2/005 600/30 |
| 2008/0051911 A1 | * | 2/2008 | Rucker .................... 623/23.7 |
| 2008/0086113 A1 | * | 4/2008 | Tenney et al. ........... 604/892.1 |
| 2008/0161837 A1 | | 7/2008 | Toso et al. |
| 2009/0076595 A1 | | 3/2009 | Lindquist et al. |
| 2009/0171377 A1 | * | 7/2009 | Intoccia et al. .......... 606/151 |
| 2009/0216317 A1 | * | 8/2009 | Cromack ............. A61L 31/16 514/1.1 |
| 2009/0285975 A1 | | 11/2009 | Bates et al. |
| 2010/0042206 A1 | * | 2/2010 | Yadav ................. A61F 2/91 623/1.42 |
| 2010/0063599 A1 | * | 3/2010 | Brunelle ............. A61L 31/044 623/23.72 |
| 2010/0105979 A1 | | 4/2010 | Hamel et al. |
| 2010/0189764 A1 | | 7/2010 | Thomas et al. |
| 2010/0239635 A1 | * | 9/2010 | McClain ............. A61L 27/16 424/423 |
| 2010/0256442 A1 | | 10/2010 | Ogdahl et al. |
| 2010/0261952 A1 | | 10/2010 | Montpetit et al. |
| 2010/0261955 A1 | | 10/2010 | O'Hern et al. |
| 2011/0077457 A1 | * | 3/2011 | Deitch ................ A61F 2/0045 600/37 |

FOREIGN PATENT DOCUMENTS

| | | |
|---|---|---|
| WO | 2010093333 A1 | 8/2010 |
| WO | WO 2011/063412 | 5/2011 |
| WO | WO 2011/072148 | 6/2011 |

OTHER PUBLICATIONS

Pavelic et al., "Liposomal gel with chloramphenicol: characterization and in vitro release," Acta. Pharm. 54 (2004) 319-330.
Glassner et al. Polymer Report, "Physical properties of poly(β-hydroxybutyrate)-poly(ε-caprolactone) blends," vol. 35, No. 10, pp. 2233-2236 (1994).
Wolf, et al., Beilstein J. Org. Chem., "Poly(glycolide) multi-arm star polymers: Improved solubility via limited arm length," vol. 6, No. 67 (2010) 9 pages.
Ko, et al., International Journal of Pharmaceutics, "Preparation and characterization of chitosan microparticles intended for controlled drug delivery," vol. 249, pp. 165-174 (2002).
Berger, et al., European Journal of Pharmaceutics and Biopharmaceutics, "Structure and interactions in covalently and ionically crosslinked chitosan hydrogels for biomedical applications," vol. 57, pp. 19-34 (2004).
Blow, N., Nature Methods, "Cell migration: our protruding knowledge," vol. 4, pp. 589-593 (2007).
Davis, et al., Biomaterials, "Photoinitiated crosslinked degradable copolymer networks for tissue engineering applications," vol. 24, pp. 2485-2495 (2003).
Extended European Search Report for EP Application No. 12748830.2, dated Oct. 18, 2016, 8 pages.

* cited by examiner

PELVIC IMPLANT AND THERAPEUTIC AGENT SYSTEM AND METHOD

PRIORITY

This application claims the benefit from International No. PCT/US2012/026325, which was granted an International filing date of Feb. 23, 2012, which in turn claims the benefit of U.S. Provisional Patent Application Ser. No. 61/445,886, filed Feb. 23, 2011, entitled PELVIC IMPLANT AND THERAPEUTIC AGENT SYSTEM AND METHOD, which applications are incorporated herein by reference in their entireties.

FIELD OF THE INVENTION

The present invention relates generally to surgical methods and apparatus and, more specifically, to surgically implantable mesh, sling or anchoring devices having one or more materials or coatings to treat incontinence or other pelvic disorders.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective implantable mesh that can be used to treat incontinence, and/or pelvic organ prolapse and other conditions.

SUMMARY OF THE INVENTION

The present invention describes pelvic mesh implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Embodiments of the implants can include a material or coating adapted to provide immediate or timed release of various therapeutic agents to treat the surrounding tissue.

In one embodiment, the invention provides a medical implant configured for placement at a pelvic location and release of a therapeutic agent, the implant comprising a multilayered film comprising three or more therapeutic agent-containing layers and two or more intermediate regulating layers that are different than the therapeutic agent-containing layers and that modulate release of the therapeutic agent from the film, each intermediate layer positioned between two therapeutic agent-containing layers.

In another embodiment, the invention provides a medical implant configured for placement at a pelvic location and release of a therapeutic agent, the implant comprising a woven or non-woven mesh comprising a plurality of apertures, wherein a portion of the apertures comprise a membrane comprising a therapeutic agent, and each aperture comprising a membrane is adjacent to at least one open aperture.

In another embodiment, a medical implant configured for placement at a pelvic location and release of a therapeutic agent, the implant comprising a strip or sheet comprising a plurality of pores that comprise one or a combination of therapeutic agent(s), wherein:

(a) the plurality of pores comprises pores having different volumes, where following implantation, to provide a prolonged therapeutic agent release profile; or (b) wherein a portion of the plurality of pores are covered with a bioabsorbable material, where following implantation, the bioabsorbable material is degraded to uncover the pores to provide a prolonged therapeutic agent release profile.

Embodiments of the present invention may be incorporated into or provided with various commercial products marketed by American Medical Systems of Minnetonka, Minn., as the MiniArc® Single-Incision Sling and like implant or anchoring systems.

DETAILED DESCRIPTION

Figure 1:
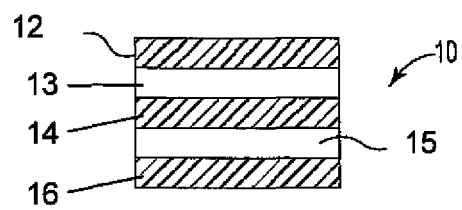
FIG. 1 shows a cross section of a multilayered polymeric construction formed of absorbable polymeric material.

Referring generally to FIGS. 1-14, various embodiments of therapeutic agent-releasing implants, such as implantable sling or mesh systems, for treatment of a pelvic tissue disorder. The pelvic implants can release therapeutic agent to provide therapeutic benefits for the surrounding tissue. Various portions of the implants can be constructed at least in part of polymer materials, such as a film or sheet material of polypropylene, polyethylene, fluoropolymers or like compatible materials. Various portions of the implants can also have absorbable materials, such as absorbable polymeric materials. The absorbable polymeric materials can be used in the implants to regulate release of the therapeutic agent, such as proving a release barrier, elution barrier, or erodible matrix from which the therapeutic agent is released.

Exemplary biologically-active components include steroid hormones such as estrogen, growth factors, pro-angiogenesis factors, anti-fibrotic agents, anti-microbial agents, antibiotics, immunosuppressive agents, inhibitors of epithelial cell activation and/or migration, compounds that enhance wound regeneration, anti-inflammatory agents, anti-cancer drugs, etc. For example, the bioactive agent can comprise the ovarian steroid, estrogen or estradiol, to treat vaginal prolapse.

Therapeutic agents having a steroid ring system are referred to as steroids, which can include naturally occurring compounds and synthetic analogues based on steroid ring structures. Steroids which can be used in the therapeutic agent-releasing implant include glucocorticoids, estrogens and androgens. Table 1 lists exemplary therapeutic agents that can be associated with and released from various embodiments of therapeutic agent-releasing implants as described herein.

TABLE 1

Therapeutic agents

1a. Steroid hormones:
Dexamethasone, cortisone, hydrocortisone, prednisone, prednisolone, triamcinolone methylprednisolone, beclomethasone, betamethasone, chloroprednisone, corticosterone, desoxycorticosterone, estradiol, fluorocortisone, androsterone, aldosterone, methyl testosterone, norethandrolone, estriol, estrone, hydroxyprogesterone;
1b. Antibiotics
Amoxicillin, ephalexin, cefadroxil, cefuroxime, loracarbef, cefixime, pivmecillinam, trimethoprim-sulfamethoxazole, trimethoprim, ofloxacin, ciprofloxacin, norfloxacin, levofloxacin, doxycycline, tetracycline, minocycline, gentamicin, tobramycin, amikacin, nitrofurantoin; azithromycin
1c. Cytotoxic/chemotherapeutic/anti-cancer/immunosuppressive agents
Doxorubicin, cisplatin, fluorouracil, chlorambucil, methotrexate, cyclophosphamide, etoposide, ifosfamide, leuprolide, mitomycin C, tamoxifen, carboplatin, paclitaxel, vinblastine, vincristine, everolimus, imiquimod, Gardasil ™ (Recombinant HPV Quadrivalent Vaccine), cetuximab, daunorubicin, bevacizumab, trastuzumab, rituximab, panitumumab;
1d. Growth factors and ECM proteins
Transforming growth factor beta (TGF-beta), platelet derived growth factor (PDGF), vascular endothelial growth factor (VEGF), collagen, fibronectin.

Various types of absorbable polymeric materials can be used to modulate release of therapeutic agent form the implants. The terms "bioabsorbable," "degradable," and "biodegradable," can also be used to describe a material that is absorbable, such as an absorbable polymer. Many absorbable polymers include hydrolytically unstable chemical groups such as ester groups in the polymeric backbone. The hydrolytic cleavage of these chemical groups leads to degradation of the polymer. Absorbable polymers, such as those described in Table 2, can be used in any of the embodiments of the invention.

TABLE 2

Absorbable or biocompatible polymers

Polyhydroxyalkanoates (e.g., poly-4-hydroxybutyrate (P4HB), poly(3-hydroxyvalerate, poly(hydroxybutyrate-co-hydroxyvalerate); polyesters (e.g., polylactic acid, poly(lactide-co-glycolide), polycaprolactone, poly(valerolactone), poly(glycolic acid), (poly(glycolide)), and poly(dioxanone); polyorthoesters; polyalkeneanhydrides (e.g., poly(sebacic acid); polyanhydrides, polyphosphazine.
Hyaluronic acid, alginate, dextran, starch, amylopectin, cellulose, xanthan, pullulan, chitosan, pectin, inulin, and heparin.

Polyhydroxyalkanoates include homopolymers such as poly-4-hydroxybutyrate (P4HB), poly(3-hydroxyvalerate), and hydroxyalkanoate copolymers such as poly(hydroxybutyrate-co-hydroxyvalerate) (Organ, S. J. (1994) Polymer, 35, 1:86-92) Blends of hydroxyalkanoate polymers with other absorbable polymers have also been prepared, such as poly(β-hydroxybutyrate) and poly(ε-caprolactone) blends (Gassner, F., and Owen, A. J. (1994) Polymer, 35, 10:2233-2236).

Poly(glycolic acid) (PGA) is a highly crystalline and has a melting point in the range of 225-230° C. While higher molecular weight forms are insoluble in common organic solvents such as acetone, dicholomethane, chloroform, and tetrahydrofuran, its lower molecular weight forms generally have better solubility in common organic solvents. Glycolide copolymers also can have better solubility in common organic solvents. For example, star block copolymers based on glycerol and glycolide show solubility in organic solvents such as DMF and DMSO (see, for example, Wolf, F. K., et al. (2010) *Beilstein J. Org. Chem.* 6, No. 67). Copolymers of lactic acid and glycolic acid (e.g., 50:50 mol percent) have solubility in chloroform (U.S. Pat. No. 3,867,190). Copolymerization of lactic acid and glycolic acid reduces the degree of crystallinity and results in an increased rate of hydration and hydrolysis. Copolymers of lactic acid and glycolic acid can be manipulated into a desired form by techniques such as extrusion, injection and compression molding as well as particulate leaching and solvent casting.

Lactic acid is a chiral molecule and L-lactide and D-lactide optically active forms can be polymerized to form poly-L-lactide (PLLA), poly-D-lactide (PDLA), and poly-D,L-lactide (PDLLA). PLLA has a crystallinity of about 37%, a glass transition temperature between 60-65° C., and a melting temperature between 173-178° C. PDLLA is amorphous and has a glass transition temperature of 55-60° C.

Another polyester, polydioxanone (PDS) is made by a ring-opening polymerization of the p-dioxanone monomer that forms a polymer of multiple repeating ether-ester units. PDS has a glass transition temperature in the range of −10 to 0° C. and a degree of crystallinity of about 55%. The presence of an ether oxygen within the polydioxanone backbone of the polymer chain can provide materials with enhanced flexibility.

Exemplary erodible polyorthoesters polyorthoesters can be formed by reacting an orthoester (or orthocarbonate) with a diol (see, for example, U.S. Pat. Nos. 4,079,038, and 4,138,344), or by reacting a reacting a polyol with a polyfunctional ketene acetal (see, for example, U.S. Pat. No. 4,304,767).

In many cases, the degradation rate of a homopolymer (i.e., one formed from a particular monomer type is) slower than copolymer (formed from the particular monomer a different monomer). Various embodiments of the invention can use copolymers and homopolymers, which share a common monomer type, to provide implants with portions having different rates of degradation.

As shown in FIG. 1, at least a portion of the implant 10 can include multiple layers. Each layer, or one or more of the layers of the implant 10 can include biologics, agents, drugs, estrogen, or like agents adapted to treat tissue. In one embodiments, the therapeutic agent can be included in alternating layers of doped and bioresorbable polymer materials. As the first layer breaks down, the doped material or agent is released into the tissue. The following layer can be void of doped material or agents to allow for tailoring of the times release of the agent. The thicker the non-doped layer, the greater amount of time between agent release. This sequence of layers may be built upon one another to achieve the desired elution profile. The bioresorbable material may be polymer-based or a biologic. In certain embodiments, various doped layers can include different agents, and the layer application may be finely controlled to dictate release and timing. Exemplary agents can include estrogen, antibiotics, anti-inflammatory, growth factors, and the like.

One embodiment of the invention provides an implant comprising a multiple-layered construct. For example, with reference to FIG. 1, the implant includes a construct that has three or more therapeutic agent-containing layers (12, 14, and 16) and two or more modulating layers (13 and 15) that are different than the therapeutic agent-containing layers. In some constructions, the modulating layers can at least regulate the release of a therapeutic agent from an inner therapeutic agent-containing layer (e.g., layer 14). Each modulating layer can be positioned between two therapeutic agent-containing layers (e.g., between outer and inner therapeutic agent-containing layers). The modulating layers may also serve one or more other functions, such as serving as a matrix material to promote adherence of cells and tissue formation.

The multiple-layered construct can use one or more absorbable polymeric materials such as those described in Table 2.

Generally, the degradation rate of a homopolymer (i.e., one formed from a particular monomer type is) slower than copolymer (formed from the particular monomer a different monomer). In some cases the multi-layered construct includes layers formed from a homopolymer and copolymer that share a common monomer, with the copolymer having a rate of degradation that is faster than the homopolymer. Faster degrading copolymers can be used in the outer layers. Some copolymer types, such as copolymers of 6-caprolactone with dl-lactide, have been synthesized to yield materials with rapid degradation rates. For example, an $\epsilon$-caprolactone-dl-lactide copolymer can be present in either or both of the outer therapeutic agent-containing layers 12 and 16, and an $\epsilon$-caprolactone homopolymer or dl-lactide homopolymer can be present in the modulating layers 13 and 15, or the inner therapeutic agent-containing layer 14.

Another way to modulate degradation rate is though molecular weight of the absorbable polymer. For example, by increasing the size of a polymer, the degradation can be slowed. Poly(D,L-lactide) preparations of different molecular weight ranges (e.g., 10,000-18,000, and 18,000-28,000), and poly(D,L-lactide-co-glycolide) preparations preparations of different molecular weight ranges (e.g., 7,000-17,000, 24,000-38,000, 38,000-54,000, 54,000-69,000) are commercially available from Sigma-Aldrich under the tradename Resomer™.

In one construction, the multiple-layered film is completely biodegradable. As a general matter, all layers of the film include one or more biodegradable material(s), such as biodegradable polymers. The film can be constructed so that the outer therapeutic agent-containing layers 12 and 16 have a rate of degradation that is faster than the rate of degradation of the modulating layers 13 and 15, and the inner therapeutic agent-containing layer 14. Absorbable polymers or polymer mixtures can be chosen based on their degradation profiles. For purposes of discussion, a polymer with a first rate of degradation in the body can be referred to herein as a "first absorbable polymer," and a polymer with a second rate of degradation in the body can be referred to herein as a "second absorbable polymer," and so on, with the first rate of degradation being more rapid than the second rate of degradation. Exemplary first and second polymer pairs can be, respectively, for example, PLGA and PLLA; PLGA and PCL; and PLGA 25K Da and PLGA 25K Da.

The degradability of the polymeric layers can also be controlled by the hydrophobic or hydrophilic nature of the material in the layer, the composition of the polymer in each layer, as well as the inclusion of other materials that can influence the rate of degradation of the polymeric layers, such as the presence of acidic or basic materials in the layers.

Optionally, the multiple-layered film can include a third polymer having a rate of degradation that is slower than either of the first of second polymers. The third polymer can be located in an inner therapeutic agent-containing layer, e.g., layer 14.

The degradation characteristics of the film and release of therapeutic agent can be determined by construction and materials of the film, including the absorbable polymer, and the type or types of therapeutic agent in the absorbable layer of the film. Release of the therapeutic agent can occur by diffusion or elution of the therapeutic agent(s) out of the therapeutic agent-containing layers, by degradation and release of the therapeutic agent coinciding with degradation of the polymeric layers, or both. For example, in modes of practice, the therapeutic agent elutes from the outer layers 12 and 16 so that it becomes available in the surrounding tissues during a first time period following implant placement. In some modes of delivery, release of the therapeutic agent from the outermost layers 12 and 16 can coincide partially, or entirely, with erosion/degradation of the outermost layers. In some cases the majority of the therapeutic agent is released from the outermost layers prior to any substantial degradation of the layers.

Release of the therapeutic agent from an inner layer (e.g., layer 14) follows release of the therapeutic agent from the outermost layers. Release of the therapeutic agent from an inner layer can coincide partially with release of the therapeutic agent from an outer layer, or there can be a period of time between when the release of therapeutic agent from the outer layers ends, and where release of the therapeutic agent from an inner layer starts. Release of the therapeutic agent from an inner layer can be delayed using the layered constructions of the invention that can result in one of various release mechanisms. For example, the modulating layers 13 and 15 can serve as barriers to slow the elution of the therapeutic agent from the inner layer 14 to the surrounding tissue. Depending on the extent of degradation of the outer layers 12 and 16, the therapeutic agent from the inner layer 14 may also be required to cross outer layer material for release from the implant. In other modes of practice degradation of the regulating layers 13 and 15 may modulate release of the therapeutic agent from the inner layer 14 by preventing its release. For example, modulating layers 13 and 15 may be impervious to the therapeutic agent of the inner layer 14, and to cause release of therapeutic agent from the inner layer 14, degradation of layers 13 and 15 occurs.

Release of the therapeutic agent from an inner layer (e.g., layer 14) can also coincide partially, or entirely with degradation of the inner layer. Release of therapeutic agent from the inner layer generally occurs during a second time period following implantation. The second time period follows the first time period, and can overlap with the first time period, or occur after the first time period. In some modes of delivery, the therapeutic agent is released from an inner layer by migrating through the modulating layers, which serve to slow the therapeutic agent's release.

In order to discuss the release profile of the bioactive agent, the time periods can be described as a time point following implantation at which 50% of the therapeutic agent originally present in the coating at implantation is released from the coating. In some modes of delivery, the first time period is in the range of weeks to months and the second time period is in the range of months to years.

Depending on the type and loading of therapeutic agent, the type or types of polymeric material in the layers, and other properties of the layers such as thickness, etc., or other chemical properties of the multi-layered film, the therapeutic agent may have a particular release profile. For example, in some modes of delivery, the therapeutic agent present in the outermost layers 12 and 16 may display a "burst" profile where the majority of the therapeutic agent is released at a time point soon after surgical implantation of the device. In some modes of treating, a "burst" of bioactive agent can be beneficial to control a tissue response that occurs immediately after implantation.

Therapeutic agent can be present in the therapeutic agent-containing layers in any desired form. For example, the therapeutic agent can be dissolved in a polymeric layer by the virtue of it being soluble in the polymeric material, or being soluble in a solvent or solvent mixture used to dissolve the polymer and form the layer. For example, estradiol is soluble in organic solvents such as ethanol (e.g., up to 2.5 mg/mL), dimethylsulfoxide (DMSO), and dimethylformamide (DMF) (up to 20 mg/mL). Ethanol is sparingly soluble in water. DMSO and DMF are useful as solvents for various polymeric materials.

Alternatively, one or more of the therapeutic agent-containing layers can include therapeutic agent in particulate form. These layers can be prepared from compositions with dissolved polymer where particles of therapeutic agent are suspended or dispersed in the composition.

A multi-layered construct degradable throughout can be prepared in one of a variety of ways. Some modes of preparing involve the sequential formation of layers to form the multi-layered construct. The method of "layering" can be formed by one or more of a variety of techniques, such as solvent casting, spraying, dipcoating, or extrusion. In some modes of practice adjacent layers are formed using solvents that have no or no appreciable mixing with each other. For example, with reference to FIG. 1, layers 12, 14, and 16 are prepared using one or more compositions where DMSO is the solvent, and layers 13 and 15 are prepared using one or more compositions where THF is the solvent. Exemplary compositions with DMSO as the solvent include absorbable polymers such as PLGA and polyothroesters. Exemplary compositions with THF as the solvent include absorbable polymers such as polyphosphazines.

In another approach, sequential formation of layers is carried out using compositions having the same solvent but containing different polymeric materials. For example, an outer layer (e.g., layer 12) is formed using a first composition containing PLGA and a therapeutic agent and THF, and then dried to remove the THF. A second composition containing a polyorthoester, a therapeutic agent and THF is then applied over the PLGA layer and the THF is quickly flashed off before the THF is able to solubilize the polyorthoester layer, to form an intermediate layer (e.g., layer 13). THF (flash point of −21° C.), and other solvents having lower flash points, can be flashed off by application of heat during the coating process, carrying out coating in a low pressure environment, or both. Other solvents with low flash points include acetone (−18° C.), diethyl ether (−45° C.), pentane (−40° C.), hexane (−7° C.), ethyl acetate (−4° C.)_. Formation of layers 14-16 can be carried out in a similar manner.

In yet another approach, sequential formation of layers is carried out using particle bombardment technique. Particle bombardment can be used to form a coated layer without having to dissolve the polymer in a solvent. For example, U.S. Pat. No. 6,803,070 describes an apparatus having an electrostatic spray nozzle adapted to direct a stream of nanoparticles suspended in a solution toward a positive outlet. A coated layer can be formed by positioning a substrate on which the coating is to be formed, such as a previously coated layer, between an electrode and the positive outlet, so that when the electrode is charged, polymeric nanoparticles are redirected from the outlet toward the electrode and onto the previously coated layer to form an adjacent coated layer.

Thickness of the resulting layer can be controlled by selecting parameters such as the concentration of the biodegradable polymeric material, the type of solvent, and the temperature that the solvent casting is performed. A very thin layer can be formed by providing a low concentration of biodegradable polymer, increasing the temperature of the casting process, or both. The applied composition can be dried to cause removal of the solvent which forms the thin polymeric layer. In many constructions, the thickness of each layer in the construct about 100 nm or greater, such as in the range of about 0.5 μm to 25 μm, or about 1 μm to 10 μm. In many constructions, the overall thickness of the multi-layered construct is in the range of about 5 μm to about 100 μm, or about 10 μm to 100 μm.

In one mode of practice, the multi-layered construct is formed by a process including a step of forming an outer layer (e.g., layer 12) by solvent casting a composition that includes a biodegradable polymeric material, a therapeutic agent, and a solvent, on a surface. An exemplary composition includes a biodegradable polyester such as PLGA and the therapeutic agent estradiol, dissolved in a solvent such as THF for forming an outer layer. Another exemplary composition includes a biodegradable polyester such as PLGA and an antibiotic such as doxycycline, tetracycline, minocycline, or azithromycin dissolved in a solvent such as water or DMSO for forming an outer layer. In exemplary embodiments, an outer layer (e.g., layer 12 or 16) has a thickness in the range about 1 μm to about 10 μm.

A modulating layer 13 can then be formed adjacent to the outer layer 12. A modulating layer can be formed by solvent casting, spray coating, or dip coating, using a composition that includes a biodegradable polymeric material, such as one that has a rate of degradation slower than the biodegradable polymeric material used to form the outer layer and a solvent, on layer 12. The solvent used to form the regulating layer preferably does not cause any substantial dissolution of the polymeric material in the outer layer 12. As such, while there may be some mixing of polymeric materials at the interface between layers 12 and 13, the materials in each of these layers remain substantially physically separated. For example, a composition that includes an absorbable polyorthoester polymer is present in an organic solvent and applied to the outer layer 12 that includes PLLA. In exemplary embodiments, a regulating layer (e.g., layer 13 or 15) has a thickness in the range of about 0.5 µm to about 3 µm, or specifically about 1 µm to about 2 µm.

An inner therapeutic agent-containing layer 14 can then be formed adjacent to the modulating layer 13. The inner therapeutic agent-containing layer can be formed by solvent casting, spray coating, or dip coating, using a composition that includes a biodegradable polymeric material, a therapeutic agent, and a solvent, on layer 13. The solvent used to form the inner layer 14 preferably does not cause any substantial dissolution of the polymeric material in the modulating layer 13. As such, while there may be some mixing of polymeric materials at the interface between layers 13 and 14, the materials in each of these layers remain substantially physically separated. The solvent used for preparing the therapeutic agent-containing layer 14 may be the same or similar to the solvent used to form outer layer 12. In some modes of practice, layer 14 is formed by a composition that includes an absorbable PLGA polymer, a therapeutic agent, and an organic solvent and which is applied to regulating layer 13. In exemplary embodiments, an inner therapeutic agent-containing layer (e.g., layer 14) has a thickness in the range of about 0.5 µm to about 25 µm, or specifically about 1 µm to about 10 µm.

Therapeutic agent present in the outer and inner therapeutic agent-containing layers can be the same or different. If the therapeutic agents are the same, then the multi-layered arrangement can be a way of extending therapeutic agent the release to later time points following implantation. In some modes of delivery, release of the particular therapeutic agent may occur in a bimodal profile.

In other embodiments therapeutic agent the outer and inner therapeutic agent-containing layers is different. If different therapeutic agents are included in the multi-layered construct, they can be chosen to address or promote different physiological or tissue responses to the implant that may occur at different times following implantation.

Regulating layer 15 and outer layer 16 can be formed using the same compositions and techniques as described for regulating layer 13 and outer layer 12, or alternatively using compositions and techniques that result in the formation of layers having similar properties to regulating layer 13 and outer layer 12.

After the multi-layered degradable construct is formed, it can be removed from the support that it was formed upon, and then processed to form an article that can be used for or incorporated into a pelvic implant. For example, in some arrangements the multi-layered construct is processed into a sheet having a certain configuration and dimensions useful for supporting tissue (such as a central support portion) in use. The sheet can then be incorporated into or associated with another part or parts of the implant, such as a support portion, an arm or strap of the implant, a tissue anchor, and the like. Alternatively, the construct can be processed into narrow strips that have a width and length, and these strips can be incorporated into or used for the construction of an implant. For example, the strips can be glued to a peripheral support portion and optionally glued together to form a mesh portion that supports a tissue.

Figure 2:
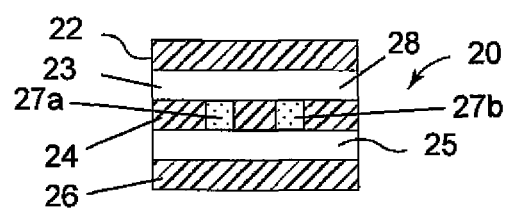
FIG. 2 shows a cross section of a multilayered polymeric construction formed of absorbable and nonabsorbable polymeric material.

In another construction, the multiple-layered film construct is partially degradable. Reference is made to FIG. 2. As a general matter, the outer layers of the film (22 and 26) are degradable and the modulating layers (23 and 25) and inner therapeutic agent-containing layer 24 are partially degradable or non-degradable. The film can be constructed so that the outer therapeutic agent-containing layers 22 and 26 have a rate of degradation that is faster than the rate of degradation of any degradable material in the modulating layers 23 and 25, or the inner therapeutic agent-containing layer 14. A first absorbable polymer having a faster rate of degradation than a second absorbable polymer can be used.

Release of therapeutic agent from the outermost layers 22 and 26 can be the same as described in relation to the outermost layers 12 and 16 of FIG. 1. The outermost layers 22 and 26 can also be formed using the procedures as described for the formation outermost layers 12 and 16 of FIG. 1.

In some aspects, the regulating layers (23 and 25) are formed partially or entirely from a biostable hydrophilic polymeric material. Exemplary hydrophilic polymeric materials include polysaccharides, poly(vinyl pyrrolidone), poly ((meth)acrylamide), and poly(urethane). The hydrophilic polymeric materials can include covalent or ionic crosslinking to provide a polymeric matrix structure for the coated layers. For example, chitosan can be crosslinked ionically or covalently using compounds such as or tripolyphosphate or glutaraldehyde, respectively (see, for example, Ko, J. A. et al. (2002) *International Journal of Pharmaceutics, Volume* 249:165-174, and Berger, J., et al. (2004) European Journal of Pharmaceutics and Biopharmaceutics Volume 57: 19-34).

In some constructions, the regulating layers (23 and 25) are prepared with pores or are constructed so that pores are formed in the layers following implantation of the construct in the body. The pores can be of a size sufficient to allow the passage of cells though the regulating layers (23 and 25). Eukaryotic cells, with are 30-50 µM in size and can fit through pores as small as 3 µM in size. Blow, N. (2007) Nature Methods, 4:589-593. Exemplary pore sizes are from about 3 to about 50 µM, about 5 to about 50 µM, about 5 to about 40 µM, about 5 to about 30 µM, or about 5 to about 25 µM.

In one mode of construction, the pores are prepared by including absorbable microparticles in the hydrophilic polymeric regulating layers (23 and 25). In this regard discrete portions of the regulating layers (23 and 25) are absorbable. For example, PLGA microparticles are dispersed in a hydrophilic polymer containing composition, and then the composition is disposed on the outer layer (e.g., 22). Generally, the microparticles used have a diameter greater than the thickness of the intermediate layer formed so the particle surface contacts the outer 22 and intermediate layer 24, when formed. Microparticle concentration can be set to form a desired number or pores per unit area in the intermediate layer.

After the multi-layered construct is introduced into the body, the microparticles are allowed to degrade. Degradation can take place while the outerlayers are degrading, or after the outer layers degrade. Degradation of the microparticles can allow the formation of pores in the intermediate layer which are of sufficient size to allow passage of cells through.

In some modes of practice, pores can be formed in a polymeric layer by creating a water-soluble thin film and lyophilizing the film. For example, polysaccharide having a low solubility can be dissolved in water or an aqueous buffer. The polysaccharide solution can be transferred to a container, forming a thin layer of solution. The solution can be placed in a shelf-lyophilizer to remove the water, leaving behind a porous, degradable scaffold.

In some aspects the modulating layers (23 and 25) can modulate release of therapeutic agent from the inner layer (e.g., 24) and also facilitate formation of new tissue in association with the implant. The hydrophilic properties of the modulating layers (23 and 25) provide a surface on which cells involved in tissue regeneration can localize. As such, the hydrophilic polymeric material of the regulating layers can serve as a cellular matrix or scaffold for the formation of new tissue.

In some modes of practice, modulating layer 23 is formed by a composition that includes a non-absorbable hydrophilic polymer such as polyacrylamide that is applied to outer layer 22. In exemplary embodiments, a regulating layer (23 or 25) has a thickness in the range of about 0.5 µm to about 25 µm, or specifically about 1 µm to about 10 µm. However, when fully hydrated the regulating layer (23 or 25) that include the hydrophilic polymeric materials can swell to about two to about three times in thickness. As such, constructs that are made using a hydrophilic polymeric material may significantly increase in thickness when placed in the body.

In some aspects the regulating layers (23 and 25) can modulate release of therapeutic agent from the inner layer (e.g., 24) and also facilitate formation of new tissue in association with the implant. The hydrophilic properties of the regulating layers (23 and 25) provide a surface on which cells involved in tissue regeneration can localize. As such, the hydrophilic polymeric material of the regulating layers can serve as a cellular matrix for the formation of new tissue.

In some constructions, the inner layer 24 includes biostable and absorbable materials. The biostable material in the inner layer 24 can serve as an adhesive to adhere regulating layer 23 to regulating layer 25. In some arrangements, with reference to FIG. 2, the biostable material is present at discreet locations that are "islands" (e.g., 27a and 27b) that serve to bridge and fasten regulating layers 23 and 25 together. Absorbable polymeric material can be present in the areas 28 of inner layer 24 that encompass the biostable material at points 27a and 27b. The absorbable polymeric material of inner layer 24 can include a therapeutic agent that is dissolved or suspended in the polymeric material of the layer.

The absorbable polymeric material of inner layer 24 can include a therapeutic agent that is dissolved or suspended in the polymeric material of the layer. Release of the therapeutic agent from an inner layer 24 follows release of the therapeutic agent from the outermost layers, and release can be the same as described with regards to the release mechanism with reference to FIG. 1.

In some modes of delivery, therapeutic agent released from the inner layer 24 migrates through or into the regulating layers 23 and 25, or both, and promotes one or more tissue regeneration processes, such as collagen deposition, granulation, cell attachment (e.g., endothelial cells and fibroblasts), cell differentiation, and angiogenesis.

For example, in some modes of practice, the therapeutic agent released from the inner layer 24 is an extracellular matrix protein such as collagen or fibronectin, or a cytokine such as transforming growth factor beta (TGF-beta), platelet derived growth factor (PDGF), and vascular endothelial growth factor (VEGF). The therapeutic agent can provide enhanced tissue growth in association with the regulating layers 23 and 25. In some cases cells can migrate into the regulating layers 23 and 25 to establish tissue formation in the material of the implant. Further, following degradation of the absorbable material of the inner layer 24, cells or other tissue forming material may fill the void between the regulating layers 23 and 25 left as a result of the degradation of the absorbable material in the inner layer 24, resulting in better tissue integration into the implant.

After regulating layer 23 is formed, in some modes of practice inner layer 24 is formed by disposition a small amount of biostable material, which serves as an adhesive, at various locations on the regulating layers 23. For example, a small volume of a composition containing hydrophilic polymer (e.g., 1-2 µL) is disposed as drops on the regulating layer 23. These drops can form bridging structures (27a and 27b) that adhere or bond regulating layer 23 to regulating layer 25. Covalent or ionic crosslinking agents can be included in the bridging structures 27a and 27b to help bond or adhere to the material of regulating layers 23 and 25. Next, a composition including degradable polymeric material and therapeutic agent is disposed around the drops of applied hydrophilic polymer to form inner layer 24, which can be formed by a process such as solvent evaporation. In exemplary embodiments, inner layer 24 has a thickness in the range of about 0.5 µm to about 25 µm, or specifically about 1 µm to about 10 µm.

After forming inner layer 24, regulating layer 25 can be formed using the same or similar method and composition as used to form regulating layer 23. After forming regulating layer 25, outer layer 26 can be formed using the same or similar method and composition as used to form outer layer 22.

Figure 13:
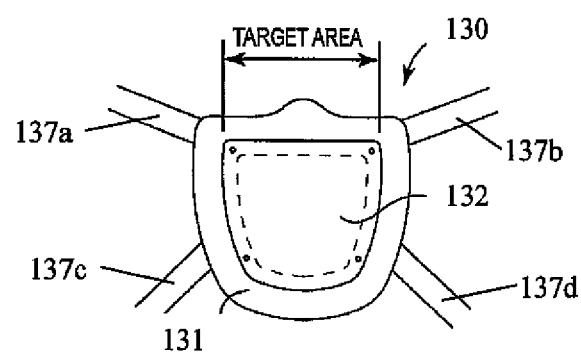
FIGS. 13 and 14 illustrate implant constructions having a central support portion and support arts extending from the central support.

The layered construct as exemplified in FIGS. 1 and 2 can be associated with a pelvic implant in various ways. FIG. 13 shows an implant having a central support portion 132, a peripheral portion 131 surrounding the central support portion 132, arms 137a-d connected to the peripheral portion 131 and which can be used to secure the implant in place by, for example, attachment to target tissue in the pelvic region. In some constructions the multi-layered construct as exemplified in FIGS. 1 and 2 is used as the central support portion 132 in the implant. The multi-layered construct can be cut to a desired shape and then secured to the peripheral portion 131 by an adhesive, or a mechanical fastener, such as a thermoplastic rivet.

Figure 14:
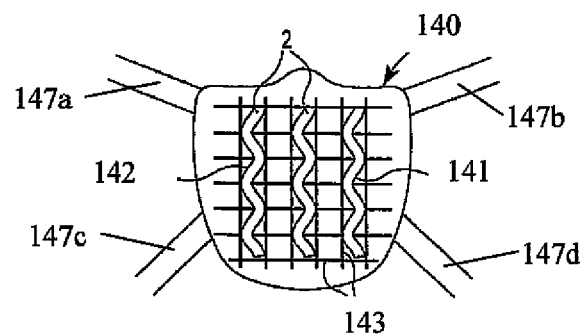

FIG. 14 shows an implant having a central support portion 141 with a mesh (woven, or non-woven/molded) as the support material. Filaments or struts of a molded support portion are represented by item 143. Arms 147a-d are connected to the central support portion 141 for securing the implant in place. In embodiment, the layered construct as exemplified in FIGS. 1 and 2 is cut into thin strips 142 and these are woven into the pre-existing mesh structure of the central support portion 141. Optionally, the ends of the 142 can be secured to a portion of the implant, such as the filaments or struts of the central support portion 141 by an adhesive, or a mechanical fastener, such as a thermoplastic rivet.

Figure 3:
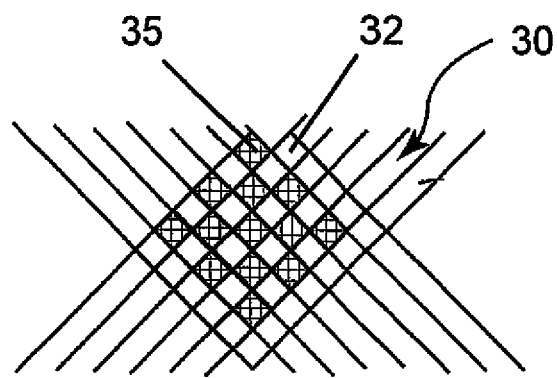
FIG. 3 illustrates a mesh construct with polymeric membranes formed in a portion of the apertures of the mesh.
Figure 4:
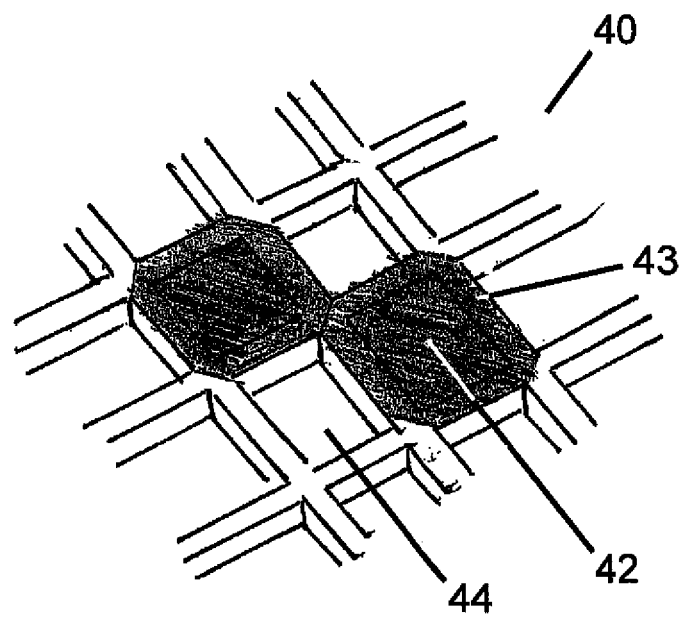
FIG. 4 illustrates a portion of a mesh construct with polymeric membranes formed in a portion of the apertures of the mesh.
Figure 5:
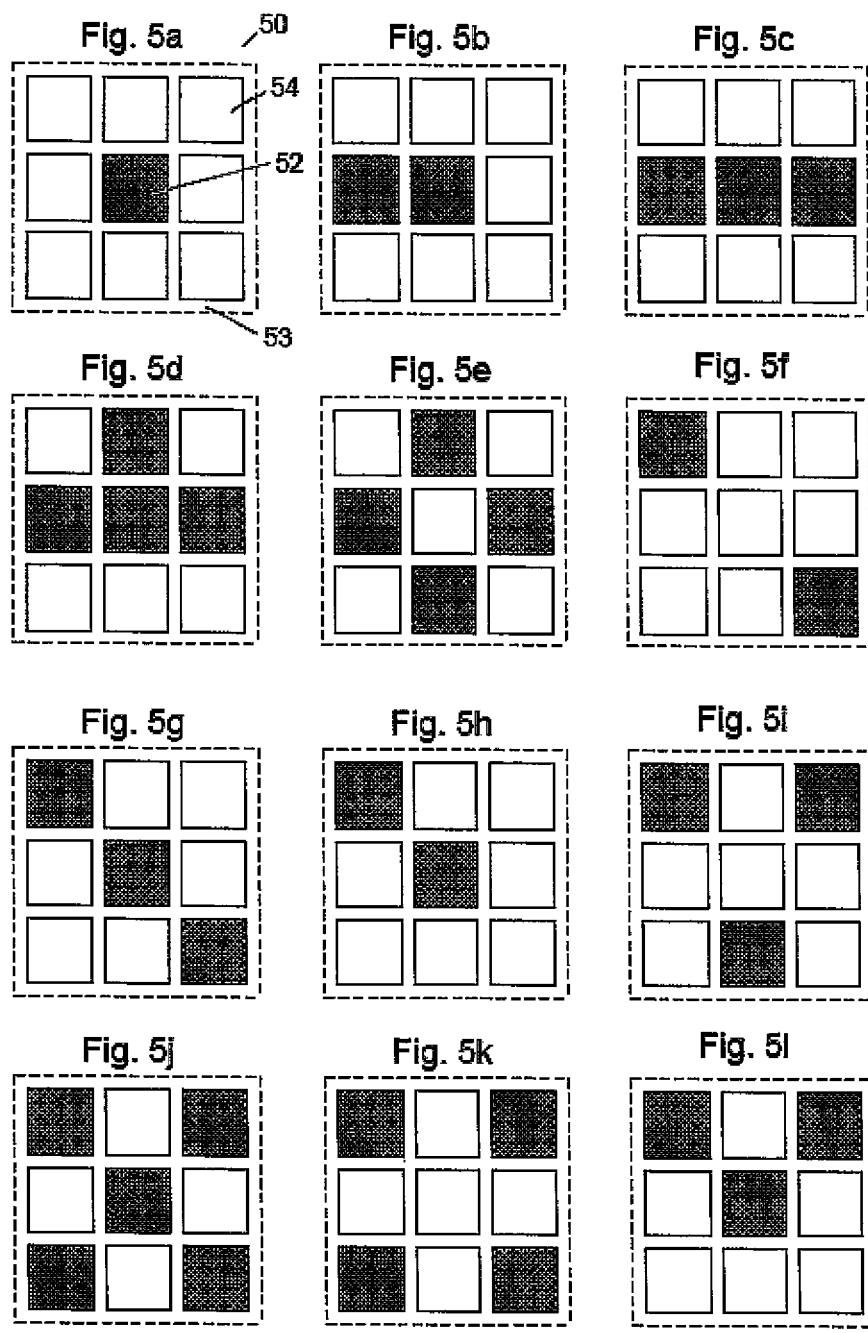
FIGS. 5a-5l illustrates portions of mesh constructs with polymeric membranes formed in a portion of the apertures of the mesh.

In other embodiments, and with reference to FIGS. 3-5, the invention provides a medical implant configured for placement at a pelvic location and release of a therapeutic agent, the implant including a woven or non-woven mesh comprising a plurality of apertures, wherein a portion of the apertures comprise a membrane comprising a therapeutic agent. In the construct, each aperture comprising a membrane is adjacent to at least one open aperture. The implant construction therefore provides open areas that promote cellular in-growth and tissue formation, and areas that are adjacent to the open areas that can release therapeutic agent and enhance tissue formation in association with the implant. For example, FIG. 3 shows a mesh 30 with an approximately equal distribution of membrane-containing apertures (e.g., 32) and unfilled apertures (e.g., 35), that form a checkered pattern in a portion of the implant.

The therapeutic agent can elute from the membrane, and degradation of the membrane can occur during or after therapeutic agent elution. The membranes with therapeutic agent can be formed in one or more areas of the mesh that treat target tissue following placement of the implant. The therapeutic agent can be added without reducing the retention and support properties of the implant (load bearing), and the membranes with therapeutic agent can be specifically tailored and repeatable.

The mesh portion can be formed from any woven or non-woven, mesh-like, construction. Exemplary materials used for the mesh include non-absorbable polymeric materials such as polyolefins such as polypropylene (PP) and polyethylene (PE); polyamides (e.g., nylons) such as polyhexamethylene adipamide or polyhexamethylene sebacamide; fluoropolymers such as polytetrafluoroethylene (PTFE) and polyvinylidene fluoride (PDF); and polyesters such as polyethylene terephthalate (PET). In some aspects, polypropylene is used as a nonabsorbable material to form the mesh. Exemplary constructions use polypropylene, including isotactic and syndiotactic polypropylene, or blends thereof, to form the mesh.

In some embodiments the implant has a knitted or woven construction using polypropylene monofilaments (see, for example, U.S. Pat. No. 4,911,165). The mesh can be constructed from a monofilament or a multifilament yarn. Exemplary monofilaments have diameters in the range of about 10 μm to about 250 μm (~0.0004 to ~0.01 inches), or more specifically from about 25 μm to about 150 μm (~0.001 to ~0.006 inches).

In other constructions the implant includes a non-knitted/non-woven (e.g., molded) polymeric mesh layer (see, for example, commonly assigned PCT Publication Nos. WO2011/063412 and WO2011/072148), such as one made from polypropylene. Non-knitted/non-woven meshes can be formed of patterned cells by way of a molding, die casting, laser etching, laser cutting, extruding, punching, or 3-D printing process. The portion of the implant that is the non-knitted/non-woven mesh can be considered a homogenous unitary construct. The pattern cut or formed implant can be constructed of a non-absorbable polymer material to provide a lattice support structure of repeated apertures or cells. Repeated apertures in the implant generally form a lattice structure and can be cut or molded into sinusoid, or other waveform or undulating strut patterns to control elongation or compression along single or multiple axes to define a desirable pattern density with overall reduced surface area, and to control the distribution and shaping from applied loads.

The size and shape of the openings in the mesh can be defined by the weave or knitting patterns of the woven mesh, or the molding pattern of the non-woven mesh. The openings can be of any one or combination of shapes, such as square, rectangular, triangular, oval, circular, or more complex polygonal shapes (hexagonal, etc.), as well as irregular shapes, such as might be associated with more complex knitted or woven constructs.

Exemplary sizes of the apertures in the mesh construct can be in the range of about 0.2 mm$^2$ to about 2 mm$^2$, or more specifically in the range of about 0.5 mm$^2$ to about 1.5 mm$^2$.

In some aspects the thickness of the non-absorbable mesh is in the range from about 0.004 inches (~0.1 mm) to about 0.020 inches (~0.58 mm).

In some cases the mesh can also be defined in terms of its basis weight. In many constructions a mesh with a lower basis weight can be more porous or have larger openings, whereas a mesh with a higher basis weight is less porous or has smaller openings. In some aspects the mesh has a basis weight in the range of 5 g/m$^2$ to about 100 g/m$^2$, and more specifically in the range of 10 g/m$^2$ to about 50 g/m$^2$, or about 15 g/m$^2$ to about 30 g/m$^2$.

Mesh porosity can also be expressed in terms of percent porosity. "Porosity" refers to the percentage of the mesh surface that has openings. Prior to forming the membranes in the mesh, the mesh preferably has porosity of greater than 50%, and more preferably greater than 60%, 70%, or 75%.

The mesh construct having a portion of the apertures that include a membrane with therapeutic agent can be formed from any one of a variety of techniques. In one method of preparing, a woven or non-woven (e.g., molded) mesh is obtained or constructed, and then a composition is applied to desired apertures. The composition is treated to form membranes which provides the mesh with a pattern where the formed membranes are in apertures individually adjacent to at least one open aperture. For example, one method involves pipetting a small amount of a membrane-forming composition in the aperture, and then treating the composition so that it forms the membrane in the filled apertures. The treatment can include allowing a solvent to evaporate off, or evaporating the solvent under vacuum, to cause solidification of the composition, and membrane formation.

The composition can also have a high viscosity to hinder its movement so any significant amount is not leaked into adjacent apertures. Viscosity of the composition can be increased by adjusting the concentration of the reagents in the composition, or including a viscosity enhancing material.

In some constructions the membranes include an erodible material that degrades over a period of time following implantation, which can coincide with or follow release of bioactive agent. Exemplary absorbable polymers, such as those listed in Table X, can be used in a composition to form the membrane. Bioactive agents, such as those listed in Table X, can be used in a composition to form the membrane.

Another method of forming the implant involves using light irradiation to cause light curing of a composition. Irradiation of the implant can be performed following placement of the composition into select apertures, which causes the composition to solidify, such as by formation or crosslinking of polymeric material. Photosensitive reagents that can be used to cause polymerization of a composition to form the membrane are commercially available (for example, Irgacure™, BASF). Exemplary photosensitive compounds initiate free radical polymerization of polymerizable material in the composition following UV exposure. Exemplary polymerizable materials include monomers and polymers (macromers) with unsaturated groups. For example, the composition can include a divinyl terminated poly(lactide-co-caprolactone) macromers which can be crosslinked in the presence of a light initiating system (see, for example, Davis, K. A. (2003) *Biomaterials* 24:2485-95).

An exemplary composition includes PLGA as the erodible matrix forming material of the membrane at a concentration in the range of 5 to 500 mg/mL, estradiol as the therapeutic agent at a concentration in the range of 0.5 to 50 mg/mL, dissolved in a solvent selected from the aprotic polar solvent category.

In some modes of practice a mask is used in conjunction with a composition that includes a light curable composition in order to form the patterned arrangement of membranes in the apertures. The mask can include openings corresponding to the locations of the apertures in the mesh where it is desired to form a membrane. In order to form the membranes in the mesh, composition can be applied over the entire surface of the mesh, or over at least a portion of the surface of the mesh where the membranes are desired to be formed. Next, the mask can be placed over the mesh and aligned so the openings in the mask align with those apertures in the mesh where membrane formation is desired. Next, light radiation can be applied to promote curing of the composition through the mask. After the membranes have formed at the desired aperture locations, the mask can be removed, and any uncured composition (e.g., if located in other apertures) can be removed, such as by washing.

With reference to FIG. 4, following drying or curing, a membrane 42 is formed in an aperture with the membrane material, such as a biodegradable polymeric matrix. The membrane material is adhered to the structural material of the mesh (e.g., a strut 43 of a molded mesh) which forms each aperture. Membrane 42-filled aperture is adjacent to open aperture 44, as well as other open apertures. The membrane can have a desired thickness, which can be controlled using the membrane-forming composition, or the process used to form the membrane.

Various membrane patterns in accordance with this embodiment are shown in FIGS. 5*a*-5*l*, in which a portion of the mesh of having nine apertures ("three squared") is shown. In FIG. 5*a*, a portion of the mesh 50, having membrane-filled aperture 52, open aperture 54, and material strut 53 of the mesh are shown, which are representative of the apertures and mesh materials of the patterned meshes of FIGS. 5*b*-5*l*. Any pattern shown in FIGS. 5*a*-5*l* can be rotated clockwise or counterclockwise to provide a desired pattern. Any of the nine aperture patterns of FIGS. 5*a*-5*l*, as shown, or rotated clockwise or counterclockwise, can be present as a sub-pattern that is repeated throughout the mesh. Different patterns can also be combined with each other to create the implant. The membrane location or locations in a three squared portion can be numerically described from top left to bottom right. For example, the pattern of FIG. 5*e* is "2-4-6-8," and the pattern of FIG. 5*j* is "1-3-5-7-9." "Adjacent" apertures share a common border or a common point. For example, in FIG. 5*a*, membrane-filled aperture #5 is adjacent to apertures 1-4 and 6-9.

The mesh of this embodiment can also be described as the percentage of the entire apertured area that is filled with membrane material. Generally, the percentage of apertures filled with membrane material in is the range of about 10% to about 60%, and more specifically in the range of about 20% to about 50%, or about 25% to about 45%.

The degradation characteristics of the membrane and release of therapeutic agent can be determined by materials used to make the membrane, including the absorbable polymer, and the type or types of therapeutic agent in the absorbable membrane. Release of therapeutic agent can occur by diffusion or elution of the therapeutic agent(s) out of the membrane, by degradation and release of the therapeutic agent coinciding with degradation of the membrane material, or both.

Release of the therapeutic agent from the membrane can improve the tissues response to the presence of the implant, and can enhance tissue in-growth into the unfilled apertures of the mesh. Tissue in growth can continue into the mesh after the membrane material has eroded after a period of implantation.

Figure 6:
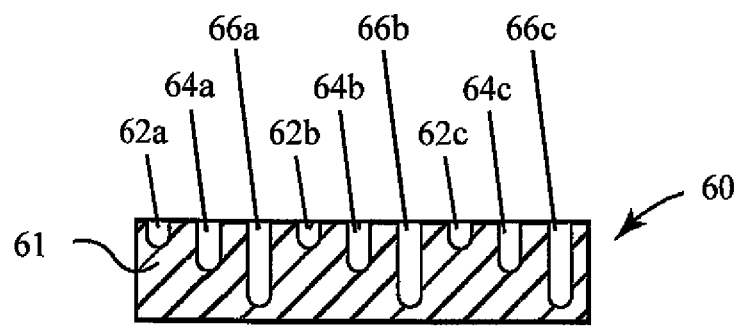
FIG. 6 shows a cross section of a strip or sheet with pores of different volumes.
Figure 7:
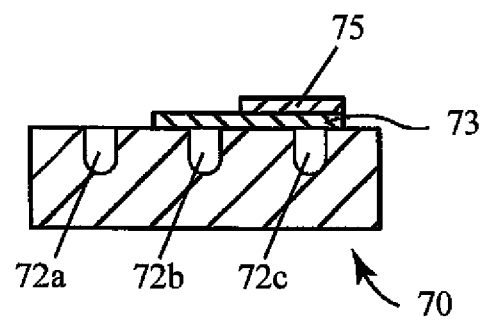
FIG. 7 shows a cross section of a strip or sheet with pores covered with polymeric layers.
Figure 8:
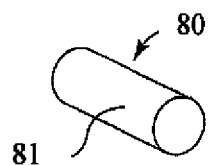
FIGS. 8-12 illustrate various monofilament constructions for use in implants.
Figure 9:
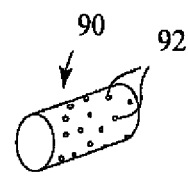
Figure 10:
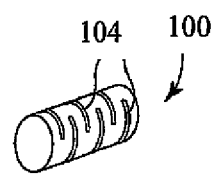
Figure 11:
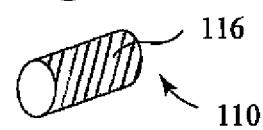
Figure 12:
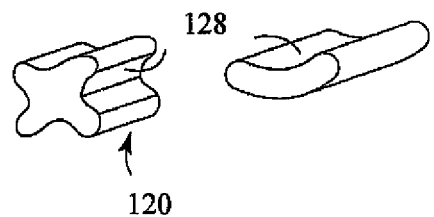

FIGS. 6-7 show other embodiments of the invention which provides a medical implant configured for placement at a pelvic location and release of a therapeutic agent, the implant comprising a strip of material having a first side comprising a plurality of pores that comprise one or a combination of therapeutic agents. In one arrangement and with reference to FIG. 6, among the plurality of pores there are pores of different volumes (e.g., 62*a-c*; 64*a-c*; and 66*a-c*). Following implantation of the device, therapeutic agent is released from the pores. Pores having greater volume are able to provide therapeutic agent release at later time points following implantation, and therefore provide a mechanism for the "long term" release of bioactive agent.

In another arrangement and with reference to FIG. 7, a portion of pores are covered with an absorbable material. Following implantation, the bioabsorbable material is degraded to uncover the pores to provide a prolonged therapeutic agent release profile.

The embodiments reflected by the constructions shown in FIGS. 6 and 7 use a strip or sheet of material (61 or 71) in which the pores are present. The strip can be prepared from a sheet of material from which thin strips of material are cut. A strip of material can be made from a thermoplastic material in which the pores can be formed, or pores can be made in the material during manufacture of the strip or sheet.

Exemplary thermoplastic materials from which the strip can be made include acrylics such as poly(acrylic acid) and poly(acrylamide), polyvinyls such as poly(ethylene), poly(propylene), poly(vinyl chloride), poly(vinyl acetate), poly(vinylidene difluoride), and poly(styrene), polyurethanes, polycarbonates, polyamides, polysulfones, polydimethylsiloxanes, and polyetherketone.

The strip/sheet can have a desired thickness suitable for use in the implant. In some constructions, the sheet has a thickness in the range of about 0.004 inches (~0.1 mm) to about 0.050 inches (~1.45 mm), or from about 0.01 inches (~0.25 mm) to about 0.025 inches (~0.72 mm).

FIGS. 6 and 7 illustrate that pores are present on one side of the strip or sheet (61 or 71). The pores can be formed into the thermoplastic material during its manufacture, or can be created after the material if formed. For example, the strip or sheet can be prepared by passing the thermoplastic material between two rolls, one of which has projecting studs to create depressions in the material, thereby forming the pores, such in a manner as described in U.S. Pat. No. 3,560,601. Other methods for preparing pores on one side of a thermoplastic sheet or strip are by drilling or boring, or by laser cutting.

As shown in FIGS. 6 and 7, the pores are present on one face of the strip or sheet, and therefore release therapeutic agent on the side the openings are formed.

With reference to the FIG. 6, Generally, the sheet or strip of this embodiment will includes pores of at least two different sizes, with the larger sized pores providing the implant with a prolonged release of therapeutic agent, as it takes a longer period of time for the therapeutic agent to be released from these pores following implantation. In some constructions, the pores in the implant individually have volumes in a desired range, such as a pore volume is in the range of about 5000 $\mu m^3$ to of about 0.1 $mm^3$, or more specifically in the range of about 50000 $\mu m^3$ to of about 0.01 $mm^3$. In exemplary construction, the sheet or strip has pores of two different volumes. In another exemplary construction, the sheet or strip has pores of three different volumes being approximately. In other exemplary constructions the sheet or strip has pores of four, five, six, or more different volumes. For example, FIG. 6 shows a strip of material 60 with pore sets of small (62a, 62b, 62c), medium (64a, 64b, 64c), and large (66a, 66b, 66c) volumes. Exemplary small pore volumes are in the range of about 7500 µm$^3$ to of about 0.025 mm$^3$. Exemplary medium pore volumes are in the range of about 15000 µm$^3$ to of about 0.055 mm$^3$. Exemplary large pore volumes are in the range of about 25000 µm$^3$ to of about 0.085 mm$^3$.

For strips or sheets that have pores with a multitude of different volumes, the pore volumes and distribution can be represented graphically.

In some cases, the implant can be described in terms of the pore volume per unit area on the strip or sheet. The pore volume per unit area can be calculated by determining the total volume in all of the pores in a certain area of the strip or sheet.

A total volume of pores can also be described. In some aspects the total volume is in the range of about 0.1 mm$^3$ to about 10 mm$^3$.

The pores in the strip or sheet can also be described in terms of shape and dimensions. As viewed from the top of the strip of sheet, the pores can be fabricated to have any desired shape, such as circular, oval, triangular, square, rectangular, hexagonal, or any regular or irregular polygonal shape. The configuration of the pore can have a pointed bottom, a flat bottom, a rounded bottom (such as shown in FIGS. 6 and 7), and the pore walls can be parallel or non-parallel. In other constructions, the pores may have irregular shapes.

The pores of the construct can then be filled with one or a combination of therapeutic agents. The therapeutic agent can be present alone or with one or more excipient components, such as stabilizers or polymeric material which can modulate the rate of therapeutic agent release. Exemplary biodegradable polymeric materials are listed in Table 2. In order to fill the pores, a composition containing a biodegradable polymer and a therapeutic agent in a solvent or solvent combination can be applied to the surface of the strip or sheet having the pore openings. The composition can then be allowed to fill the pores, or pushed into the pores with a tool in a spatula-like manner. In some modes of practice, compositions with different therapeutic agents can be used to fill the subsets of the pores.

The sheet or strip of the embodiment shown in FIG. 7 includes pores (72a-c), at least a portion of which are covered with a layer of degradable material 73. The degradable material provides a mechanism for prolonged release of therapeutic agent. After a period of implantation the erodible material is removed from the surface of the strip or sheet and allows body fluid to access the previously covered pore openings. Alternatively, or in addition to degradation, the erodible layer can provide a barrier to slow elution of therapeutic agent from the covered pores.

The pores of the strip or sheet of material covered with an erodible polymeric layer can be the same volume, or can be of different volumes. Pores of the embodiment represented by the construct shown in FIG. 7 can have volumes in a desired range, such as a pore volume is in the range of about 5000 µm$^3$ to of about 0.1 mm$^3$, or more specifically in the range of about 50000 µm$^3$ to of about 0.01 mm$^3$.

The pores (72a-c) of the construct represented by FIG. 7 can then be filled with one or a combination of therapeutic agents. The therapeutic agent can be present alone or with one or more excipient components, such as stabilizers or polymeric material which can modulate the rate of therapeutic agent release. In order to fill the pores, a composition containing a therapeutic agent in a solvent or solvent combination can be applied to the surface of the strip or sheet having the pore openings, such as described with reference to the construct of FIG. 6. In some modes of practice, compositions with different therapeutic agents can be used to fill the subsets of the pores of the construct represented in FIG. 7.

After the pores 72a-c are filled with therapeutic agent, a layer of absorbable material 73 such as described in Table X, is formed on the strip or sheet to cover at least a portion of the openings of the pores. The layer 73 can be can be formed by one or more of a variety of techniques, such as solvent casting, spraying, dipcoating, or extrusion. In exemplary embodiments, the first polymeric layer 73 has a thickness in the range of about 0.1 µm to about 25 µm, or specifically about 1 µm to about 10 µm. The first polymeric layer can cover all the openings of the pores on the surface, or a portion of the pores. If a portion of the pores are covered, this portion can be described in terms of, for example, the percentage of pores on the surface that are covered, or the percentage volume of the pores that are covered. For example, in some cases about 25% to about 90% of the total pore volume is covered by the first polymeric layer, or more specifically about 45% to about 75% of the total pore volume is covered by the first polymeric layer.

One or more additional polymeric layers can be used in conjunction with the first polymeric layer. For example, a second polymeric layer (e.g., layer 75) can be formed on top of the first polymeric layer 73. The second polymeric layer 75 can have the same thickness as the first polymeric layer, or can have a thickness in the range as described for the first polymeric layer 73. The first and second polymeric layers can be formed from the same or different polymeric materials. In some constructions, the second polymeric layer 75 partially covers the first polymeric layer 73. For example, in some cases about 25% to about 75% of the first polymeric layer 73 is covered by the second polymeric layer 75, or more specifically about 40% to about 60% of the first polymeric layer 73 is covered by the second polymeric layer 75. Additional polymeric layers, (e.g., third, fourth, etc.) may be present and formed successively on top of each other. Layers of progressively smaller area can be formed on top of each other to provide a stepped arrangement of coating material on the strip or sheet surface.

In some arrangements, the successive layering of polymeric materials provides a mechanism to slow the release of therapeutic agent from the strip of sheet. In some cases, the layers can be formed from the same polymeric material. In other cases, the layers have different polymeric materials. Preferably, if different polymeric materials are used, those polymers having a slower rate of erosion are used closer to the surface of the strip of sheet (e.g., in layer 73). In an exemplary embodiment, the construct has a first coated layer 73 including a PLGA polymer, and second coated layer 75 including a PLLA polymer.

Referring back to FIG. 6, following placement of the implant at a location in the pelvic region, therapeutic agent begins to be released from the pores (e.g., 62a-c; 64a-c; and 66a-c). Release of the therapeutic agent coincides with its depletion from the pores, and after a period of time the pores of smallest volume 62a-c are depleted of therapeutic agent, such as within a period of days to weeks. Since pores 64a-c and 66a-c have greater volumes, it takes longer to deplete the increased quantities of therapeutic agent, and therefore therapeutic agent is prolonged, such as up to weeks or months.

Referring to FIG. 7, following placement of the implant at a location in the pelvic region, therapeutic agent begins to be released from the pores that are not covered by a polymeric layer (e.g., 72a). Release of therapeutic agent from pore 72b is hindered or prevented by polymeric layer 73. For example, the polymeric layer may provide a barrier to the elution of the therapeutic agent, or degradation of the polymeric layer 73 may be needed for release to occur. Release of therapeutic agent from pore 72c, which is covered by polymeric layers 73 and 75 is hindered to a greater extent, thereby causing release to be delayed to even greater time points.

The pore-containing construct as exemplified in FIGS. 6 and 7 can be associated with a pelvic implant in various ways. FIG. 13 shows an implant having a central support portion 132, a peripheral portion 131 surrounding the central support portion 132, arms 137a-d connected to the peripheral portion 131 and which can be used to secure the implant in place by, for example, attachment to target tissue in the pelvic region. In some constructions the multi-layered construct as exemplified in FIGS. 6 and 7 is used as the central support portion 132 in the implant. The multi-layered construct can be cut to a desired shape and then secured to the peripheral portion 131 by an adhesive, or a mechanical fastener, such as a thermoplastic rivet.

FIG. 14 shows an implant having a central support portion 141 with a mesh (woven, or non-woven/molded) as the support material. Filaments or struts of a molded support portion are represented by item 143. Arms 147a-d are connected to the central support portion 141 for securing the implant in place. In embodiment, the layered construct as exemplified in FIGS. 6 and 7 is cut into thin strips 142 and these are woven into the pre-existing mesh structure of the central support portion 141. Optionally, the ends of the 142 can be secured to a portion of the implant, such as the filaments or struts of the central support portion 141 by an adhesive, or a mechanical fastener, such as a thermoplastic rivet.

In other aspects, and with reference to FIGS. 8-12, the implant includes a filament having pores or recesses are formed in a filament, and these pores or recesses are then filled with one or more therapeutic agents. Therapeutic agents, such as those described in Table 1, can be used to fill pores or recesses in the filament.

The filaments can include pores (e.g., item 92, FIG. 9), grooves (e.g., item 104, FIG. 10), surface contours (e.g., item 116, FIG. 11), cracks, pits, deformations (e.g., item 128, FIG. 12), protrusions, etc., to serve as regions to capture and contain a therapeutic agent. The filaments can be of different geometries, cross-sections, configurations, and the like. The surface configurations on the filament can be introduced with the using chemical, mechanical, electrical, laser, or other techniques available in the art.

In some aspects, the filament includes pores or recesses having at least two different volumes. Following implantation of the device, therapeutic agent is released from the pores of the filament. Similar to the embodiment exemplified by the construct of FIG. 6, pores or recesses having greater volume are able to provide therapeutic agent release at later time points following implantation, and therefore provide a mechanism for the "long term" release of bioactive agent.

In other aspects, after therapeutic agent has been introduced into the recesses or the pores of the filament, a coating can be applied over the filament to cover the therapeutic agent and to modulate its release in the body. In some aspects, the coating includes an absorbable polymer, such as one listed in Table 2. In more specific aspects, the filament has a first coated layer that surrounds the filament, and a second coated layer in contact with the first coated layer, but that only cover a portion of the filament. Therapeutic agent residing under the two coated layers can be released at later time points following implantation. The mode of release is therefore similar to the embodiment exemplified by the construct of FIG. 7, in which the successive layering of polymeric materials provides a mechanism to slow the release of therapeutic agent.

The therapeutic agent releasing constructs as described herein can be used in association with known implant and repair systems (e.g., for male and female), including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2010/0105979, 2002/151762 and 2002/147382. Accordingly, the above-identified disclosures are fully incorporated herein by reference in their entirety.

For example, some embodiments, the implant is configured for implantation into a female patient. Portions of the implant can have features to support an anatomical structure in the pelvis (i.e., a "support portion"), such as the vagina, bladder, urethra, or levator ani. Portions of the implant can also have features, such as straps or arms that extend from a support portion of the implant, or tissue anchors or fasteners (e.g., self-fixating tips), to help maintain the implant at a desired anatomical location in the pelvis.

For example, the implant can be used for treating urinary incontinence in a female subject, the implant including a urethral sling having a central portion and first and second ends or arm. The first and second ends/arms are coupled to and extend from the central support portion. Following implantation, the arms are used to help secure or position the implant at a desired anatomical location in the pelvis.

Implants of the invention can be part of a kit. The kit can include components for carrying out procedures for the insertion of the implant in a patient. Exemplary components can include tissue fasteners, tools for introducing the implant into a patient using a surgical insertion procedure, scalpels or knives for making the incision, and needles and suture material for closing the incision. All or parts of the kit can be sterilely packaged. Insertion tools useful for insertion of the implant can include a handle and an elongate needle, wire, or rod extending from the handle. The needle, wire, or rod can be shaped (such as helical, straight, or curved) to be useful to carry the implant through a desired tissue path in the pelvic region.

The particular features of the implant embodiments of the invention can be adapted to known implant constructions useful for treating female pelvic conditions, including those already described in the art. Those skilled in the art will recognize that various other mesh configurations, such as those described herein with reference to the following publications, can also be used in conjunction with the features and procedures of the current invention.

In some constructions, the implant is used for treating incontinence, prolapse, or a mixture of incontinence and prolapse, and includes a portion useful to support the urethra or bladder neck to address urinary incontinence, such as described in commonly assigned application published as US 2010/0256442 (Ogdahl, et al.), and exemplified by the mesh constructions of FIGS. 3B and 3C therein. The implant can be in the form of a mesh strip that in inserted transvaginally and used to support the urethra or bladder neck. The implant can be configured to have a length (distance between distal ends, e.g., self-fixating tips, of extension portions) to extend from a right obturator foramen to a left obturator foramen, (e.g., from one obturator internus muscle to the other obturator internus muscle). Exemplary lengths of an implant or implant portion for extension below the urethra, between opposing obturator foramen, from distal end to distal end of the extensions while laying flat, can be in the range from about 6 to 15 centimeters, e.g., from 7 to 10 centimeters or from 8 to 9 centimeters or about 8.5 centimeters. (Lengths L1 and L2 of FIGS. 3B and 3C can be within these ranges.) The lengths are for female urethral slings, and are for anterior portions of implants for treating female prolapse or combined female prolapse and incontinence, which include an anterior portion that has a length between ends of anterior extensions portions within these same ranges. A width of the extension portion can be as desired, such as within the range from about 1 to 1.5 centimeters. The implant can also have two or more tissue anchoring features (e.g., self-fixating tips). The self-fixating tips can be present at the ends of the mesh strips, or at the ends of arms or extensions that extend from a central support portion.

In some constructions, the mesh can be configured to treat pelvic conditions by supporting levator muscle, such as described in commonly assigned application published as US 2010/0261952 (Montpetit, et al.). The levator musculature or "levator ani" can include the puborectalis, pubococcygeus, iliococcygeus. Exemplary implants can be of a size and shape to conform to levator tissue, optionally to additionally contact or support other tissue of the pelvic region such as the anal sphincter, rectum, perineal body, etc. The implant can be of a single or multiple pieces that is or are shaped overall to match a portion of the levator, e.g., that is circular, oblong trapezoidal, rectangular, that contains a combination of straight, angled, and arcuate edges, etc. The implant can include attached or separate segments that fit together to extend beside or around pelvic features such as the rectum, anus, vagina, and the like, optionally to attach to the feature. The implant can include a tissue support portion, which at least in part contacts levator tissue. Optionally, the implant can additionally include one or more extension portion(s) that extends beyond the tissue support portion and to be secured to tissue of the pelvic region, for support of the tissue support portion. Optionally, extension portions can include features such as a tissue fastener (e.g., self-fixating tip, soft tissue anchor, bone anchor, etc.), a sheath, a tensioning mechanism such as a suture, an adjustment mechanism, etc.

According to exemplary methods, an implant for supporting levator muscle can be introduced through a vaginal incision that allows access to levator tissue. The method can include use of an insertion tool designed to reach through a vaginal incision, through an internal tissue path and to then extend through a second external incision. In some cases a tools is used to place a self-fixating tip at an internal location of the pelvic region, the tool length sufficient to reach from a vaginal incision to an obturator foramen, region of the ischial spine, sacrospinous ligament, or other location of placing a self-fixating tip. Exemplary methods include steps that involve creating a single medial transvaginal incision and dissecting within a plane or region of dissection including the ischorectal fossa. An implant can be inserted to contact tissue of the levator, over a desired area. A kit with the implant can include connectors for engagement between a needle of an insertion tool and a distal end of an extension portion, as well as helical, straight, and curved needles. An embodiment of a kit, including an insertion tool and an implant, is shown in FIG. 5 of US 2010/0261952.

The implant can include self-fixating tips designed to engage a distal end of an insertion tool to allow the insertion tool to place the self-fixating tip at a desired tissue location by pushing. For example, the mesh can be implanted by creating a single medial transvaginal incision under the mid-urethra, dissecting a tissue path on each side of the incision, passing a urinary incontinence sling through the incision whereby the urinary incontinence sling is suspended between the obturator internus muscles and the sling body is positioned between the patient's urethra and vaginal wall to provide support to the urethra. Commonly assigned application published as US 2011/0034759 (Ogdahl, et al.), also describes implants that include a self-fixating tip at a distal end of one or more extension portions, and transvaginal methods for inserting the mesh into a patient.

In some constructions, the mesh can be configured to treat vaginal prolapse, including anterior prolapse, posterior prolapse, or vault prolapse such as described in commonly assigned application published as US 2010/0261955-A1 (O'Hern, et al.). The mesh can be inserted transvaginally, following a single incision in the vaginal tissue, with no external incision. The mesh can be used to provide Level 1 support of the vaginal apex in combination with Level 2 support of medial vaginal sidewall tissue. In terms of vaginal prolapse, Level 1 vaginal tissue support relates to support of the top portion, or "apex" of the vagina. This section of tissue is naturally supported by the cardinal ligament that goes laterally to the ischial spine and crosses over medially to the sacrospinous ligament, and also by the uterosacral ligament that anchors into the sacrum. Level 2 support of vaginal tissue is support of tissue of the mid section of the vagina, below the bladder. This tissue is partially supported by the cardinal ligament but is predominantly supported by lateral fascial attachments to the arcus tendineus or white line. Level 3 support is that of the front end (sometimes referred to as the "distal" section) of the vagina right under the urethra. Natural support includes lateral fascial attachments that anchor into the obturator internus muscle.

The method for inserting the implant for treating vaginal prolapse can include providing an implant that includes a tissue support portion and two or more extension portions; placing the tissue support portion in contact with vaginal tissue to support the vaginal tissue; and extending a posterior extension portion to engage a sacrospinous ligament, and extending a lateral extension portion to engage tissue at a region of ischial spine, or extending a posterior extension portion to engage a sacrospinous ligament, and extending an anterior extension portion to engage an obturator foramen, or extending an extension portion to engage a sacrospinous ligament to provide Level 1 support, and supporting vaginal tissue to provide Level 2 support. FIG. 16 of US-2010-0261955-A1 illustrates a kit with an implant having a support portion piece, two extension portion pieces, adjusting tool, grommet management tool, and insertion tool.

In some modes of practice, the implants of the invention can be used along with an expansion member in a sacral colpopexy is a procedure for providing vaginal vault suspension, such as described in commonly assigned International Application No. PCT/US11/53985. A sacral colpopexy generally involves suspension, such as by use of a mesh strip implant, of the vaginal cuff to a region of sacral anatomy such as the sacrum (bone itself), a nearby sacrospinous ligament, uterosacral ligament, or anterior longitudinal ligament at the sacral promontory. The implant can be utilized in a transvaginal sacral colpopexy (TSCP) procedure with an expansion member to access tissue of the posterior pelvic region.

What is claimed is:

1. A pelvic implant configured for placement at a pelvic location and release of a therapeutic agent, the pelvic implant comprising:

at least one arm member; and a central support portion coupled to the at least one arm member, the central support portion including a multilayered film including a first outer therapeutic agent-containing layer, a second outer therapeutic agent-containing layer, an internal therapeutic agent-containing layer, a first regulating layer disposed between the first outer therapeutic agent-containing layer and the internal therapeutic agent-containing layer, and a second regulating layer disposed between the second outer therapeutic agent-containing layer and the internal therapeutic agent-containing layer, the first outer therapeutic layer having a rate of degradation that is faster than a rate of degradation of either of the first regulating layer and the second regulating layer, the internal therapeutic agent-containing layer including an absorbable polymeric material and islands of hydrophilic polymer configured to adhere to the first regulating layer and the second regulating layer.

2. The pelvic implant of claim 1, wherein the first regulating layer and the second regulating layer are configured to slow an elution of the therapeutic agent from the internal therapeutic agent-containing layer.

3. The pelvic implant of claim 1, wherein the internal therapeutic agent-containing layer has a rate of degradation slower than the rate of degradation of the first regulating layer and the second regulating layer.

4. The pelvic implant of claim 1, wherein the first and second outer therapeutic agent-containing layers comprise an aliphatic polyester copolymer or a polyorthoester.

5. The pelvic implant of claim 1, wherein the internal therapeutic agent-containing layer and the first and second regulating layers comprise an aliphatic polyester homopolymer.

6. The pelvic implant of claim 1, wherein the first and second outer therapeutic agent-containing layers are absorbable, the internal therapeutic agent-containing layer is partially absorbable, and the first and second regulating layers are non-absorbable, or partially absorbable.

7. The pelvic implant of claim 1, wherein the first and second regulating layers comprise a polymeric material selected from the group consisting of crosslinked poly(vinyl pyrrolidone), poly((meth)acrylamide), poly(urethane), hyaluronic acid, alginate, dextran, starch, amylopectin, cellulose, xanthan, pullulan, chitosan, pectin, inulin, and heparin.

8. The pelvic implant of claim 1, wherein the first and second regulating layers comprise pores having a size of 3 µm or greater.

9. The pelvic implant of claim 1, further comprising:

a peripheral portion surrounding the central support portion, the at least one arm member extending from the peripheral portion, wherein the peripheral portion is coupled to the multilayered film by a coupling member.

10. The pelvic implant of claim 9, wherein the coupling member includes an adhesive or mechanical fastener.

11. The pelvic implant of claim 1, wherein the central support portion includes a mesh, and the multi-layered film includes a first strip and a second strip, wherein the first strip and the second strip are woven through the mesh of the central support portion.

12. A pelvic implant configured for placement at a pelvic location and release of a therapeutic agent, the pelvic implant comprising:

a woven or non-woven mesh comprising a plurality of apertures along the pelvic implant in a first direction and a plurality of apertures along the pelvic implant in a second direction, the second direction being perpendicular to the first direction, wherein a portion of the plurality of apertures are filled with membranes, wherein the plurality of apertures along the implant in the first direction comprises a first membrane-filled aperture and a second membrane-filled aperture, the first membrane-filled aperture being separated from the second membrane-filled aperture by only one open aperture, wherein the plurality of apertures along the pelvic implant in the second direction comprises a third membrane-filled aperture and a fourth membrane-filled aperture, the third membrane-filled aperture and the fourth membrane-filled aperture being separated by only one open aperture.

13. The pelvic implant of claim 12 wherein sizes of the apertures in the mesh are in a range of about 0.2 mm$^2$ to about 2 mm$^2$.

14. The pelvic implant of claim 12 wherein one or more of the membrane-filled apertures include a photosensitive compound.

15. The pelvic implant of claim 12 wherein the membrane-filled apertures are in a range of about 10% to about 60% of a total amount of apertures in the pelvic implant.

* * * * *